United States Patent
Thomas

(10) Patent No.: US 8,979,877 B2
(45) Date of Patent: *Mar. 17, 2015

(54) CATHETER FOR USE IN REVASCULARIZATION PROCEDURES AND METHOD OF USING SAME

(75) Inventor: Jeffrey E. Thomas, Hillsborough, CA (US)

(73) Assignee: Neurodynamics, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/371,703

(22) Filed: Feb. 13, 2012

(65) Prior Publication Data

US 2012/0203163 A1    Aug. 9, 2012

Related U.S. Application Data

(63) Continuation-in-part of application No. 13/175,692, filed on Jul. 1, 2011.

(60) Provisional application No. 61/361,185, filed on Jul. 2, 2010.

(51) Int. Cl.
     *A61B 17/22*      (2006.01)
     *A61B 17/3207*      (2006.01)
     *A61M 25/00*      (2006.01)

(52) U.S. Cl.
CPC ............ *A61B 17/320758* (2013.01); *A61B 2017/22038* (2013.01); *A61B 2017/22079* (2013.01);

(Continued)

(58) Field of Classification Search
USPC ............. 604/19, 22; 606/108, 159, 167, 606/169–171, 198, 200; 623/1.11
See application file for complete search history.

(56) References Cited

U.S. PATENT DOCUMENTS 4,576,162 A * 3/1986 McCorkle .............. 606/159
5,443,443 A * 8/1995 Shiber .............. 604/22

(Continued)

OTHER PUBLICATIONS

Ribo, et al. "Buying Time for Recanalization in Acute Stroke: Arterial Blood Infusion Beyond the Occluding Clot as a Neuroprotective Strategy", The American Society of Neuroimaging, Journal of Neuroimaging vol. 19 No. 2, Apr. 2009 pp. 188-190.

(Continued)

*Primary Examiner* — Ashley Fishback
(74) *Attorney, Agent, or Firm* — Benesch Friedlander Coplan & Aronoff LLP

(57) ABSTRACT

A method of removing vascular blockage includes providing a catheter system comprising an outer catheter with a serrated cutting element at its distal end, a bypass catheter, and a guidewire. In the catheter system, the bypass catheter is slidably disposed within the outer catheter. The method includes positioning a distal portion of the catheter system at a proximal end of an occlusion located within a vessel and moving the bypass catheter through the occlusion so that a medicated treatment solution may be delivered through the bypass catheter to an area of the brain or other tissue served by the vessel blocked by the occlusion. Both during and after the delivery of medicated treatment solution to the blocked part of the vessel with the bypass catheter, the physician may engage the occlusion with the cutting element by moving the outer catheter in a clockwise/counterclockwise or forward/backward direction within the outer catheter, cutting and then removing at least a portion of the occlusion from the vessel.

15 Claims, 15 Drawing Sheets

(52) U.S. Cl.
CPC ..... *A61B2017/22084* (2013.01); *A61M 25/007* (2013.01); *A61M 2025/0004* (2013.01); *A61M 2025/0057* (2013.01)
USPC ........................................................ 606/159

(56) References Cited

U.S. PATENT DOCUMENTS

| | | | |
|---|---|---|---|
| 6,165,199 | A | 12/2000 | Barbut |
| 6,183,469 | B1 * | 2/2001 | Thapliyal et al. ............... 606/41 |
| 6,206,900 | B1 | 3/2001 | Tabatabaei et al. |
| 6,295,990 | B1 | 10/2001 | Lewis et al. |
| 6,416,490 | B1 | 7/2002 | Ellis et al. |
| 6,435,189 | B1 | 8/2002 | Lewis et al. |
| 6,524,300 | B2 | 2/2003 | Meglin |
| 6,730,104 | B1 | 5/2004 | Sepetka et al. |
| 2002/0151918 | A1 | 10/2002 | Lafontaine et al. |
| 2003/0097094 | A1 | 5/2003 | Ouriel et al. |
| 2005/0209665 | A1 * | 9/2005 | Hunter et al. .................. 607/115 |
| 2006/0134599 | A1 * | 6/2006 | Toner et al. ......................... 435/4 |
| 2007/0032808 | A1 | 2/2007 | Anwar et al. |
| 2009/0270888 | A1 | 10/2009 | Patel et al. |

OTHER PUBLICATIONS

International Search Report and Written Opinion, dated May 15, 2013, PCT/US2013/025878, pp. 1-1.

* cited by examiner

CATHETER FOR USE IN REVASCULARIZATION PROCEDURES AND METHOD OF USING SAME

RELATED APPLICATIONS

This application is a continuation-in-part of U.S. patent application Ser. No. 13/175,692, filed on Jul. 1, 2011 and entitled Catheter for Use in Revascularization Procedures and Method of Using Same, which claims priority to U.S. Provisional Patent Application No. 61/361,185, filed on Jul. 2, 2010, entitled Catheter for Use in Revascularization Procedures.

FIELD OF THE INVENTION

This application relates in general to a revascularization catheter system and method for treating blockage or clots in cerebral blood vessels. Specifically, this application relates to a coaxial catheter system that combines a rotational cutting mechanism over a guidewire with an aspiration mechanism for retrieving clot debris and method to bypass the clot in order to prolong the patency of the patient's vessel.

BACKGROUND

Immediately following an acute stroke, it may be necessary to reopen an occluded cerebral blood vessel, preferably within eight hours from the initial occlusion. Manipulation of the endothelium of a cerebral blood vessel is attended by adherence of platelets, which stick to the site of injury, and subsequently release clotting factors that act as chemoattractants, both binding platelets together and provoking more clotting proteins from the blood. The result of this mechanism (platelet aggregation and activation) is the accumulation of platelets and their binding together at the site as a "white thrombus," i.e. fibrin/platelet thrombus, which rapidly re-occludes the blood vessel. In this situation, a thrombolytic agent such as tPA will no longer be effective, as it has no activity against this different type of thrombus. Thus, conventional methods of removing occlusions in a blood vessel may not be adequate in all situations.

BRIEF SUMMARY

A method of removing vascular blockage includes providing a catheter system comprising an outer catheter with a serrated cutting element at its distal end, a bypass catheter, and a guidewire. In the catheter system, the bypass catheter is slidably disposed within the outer catheter. The method includes positioning a distal portion of the catheter system at a proximal end of an occlusion located within a vessel and moving the bypass catheter through the occlusion so that a medicated treatment solution may be delivered through the bypass catheter to an area of the brain or other tissue served by the vessel blocked by the occlusion. Both during and after the delivery of medicated treatment solution to the blocked part of the vessel with the bypass catheter, the physician may engage the occlusion with the cutting element by moving the outer catheter in a clockwise/counterclockwise or forward/backward direction within the outer catheter, cutting and then removing at least a portion of the occlusion from the vessel.

The peripherally-disposed outer catheter may include a distal portion having perforations. As the occlusion is removed, the distal portion of the outer catheter may be delivered to the area of occlusion, remaining within the occlusion to a varying degree, or entirely, enabling the physician to deliver medication through the perforations to a greater surface area of the occlusion.

DESCRIPTION OF THE DRAWINGS

The accompanying drawings, which are incorporated in and constitute a part of the specification, illustrate various example systems, methods, and so on, that illustrate various example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

DETAILED DESCRIPTION

Figure 1:
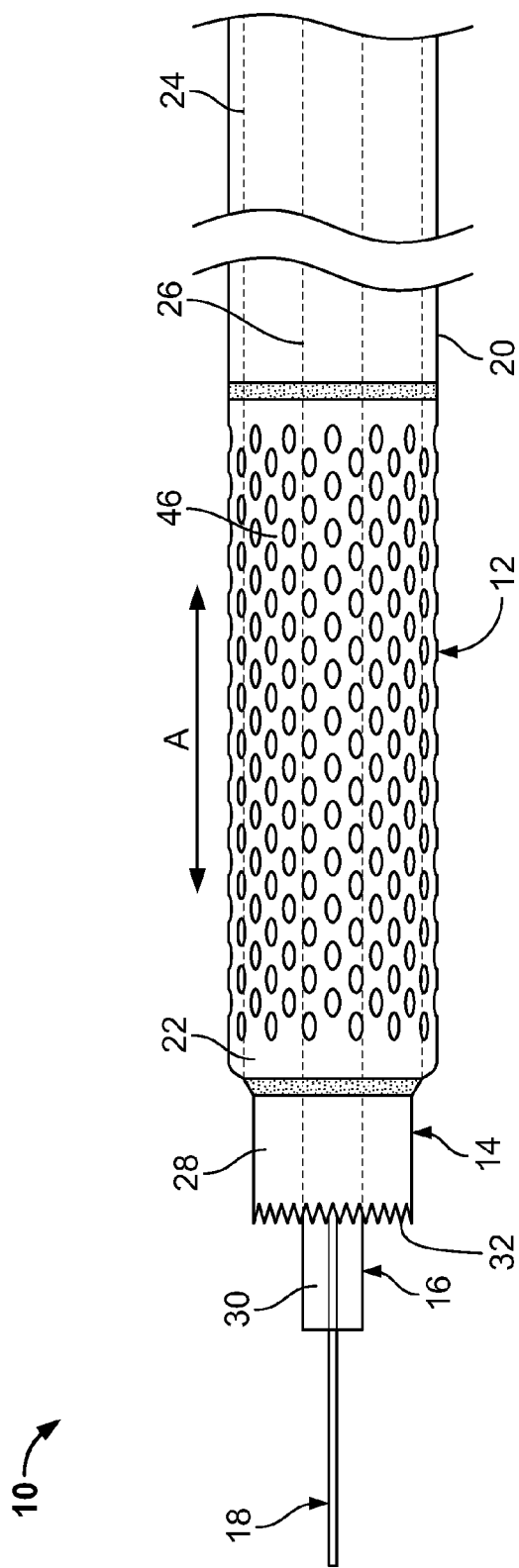
FIG. 1 is a side view of a coaxial revascularization catheter.

A revascularization catheter system 10 may be introduced into a patient suffering from an ischemic stroke in order to quickly and efficiently restore blood flow to an occluded area in a cerebral blood vessel, for example. Generally, the revascularization catheter system 10, as shown in FIG. 1, consists of a coaxial arrangement of tubular members over a guidewire. In one embodiment, the revascularization catheter system 10 includes an outer catheter 12, a cutting catheter 14, a bypass catheter 16, and a guidewire 18. The outer catheter 12 includes a generally tubular body including a proximal portion 20, a transition portion (not shown), and a distal portion 22.

Similarly, the cutting catheter 14 and the bypass catheter 16 are comprised of generally tubular bodies including proximal portions 24 and 26, respectively, transition portions (not shown), and distal portions 28 and 30, respectively. Each catheter has at least one lumen therein extending from the distal portions 22, 28, and 30 of the tubular bodies to the proximal portions 20, 24, and 26 of the tubular bodies.

The bypass catheter 16 is disposed within the cutting catheter 14 and is movable, rotatable, or slidable within the cutting catheter 14. Similarly, the cutting catheter 14 is disposed within the outer catheter 12 and is rotatable in a clockwise/counterclockwise direction and slidable in a forward/backward direction within the outer catheter 12 along a horizontal axis A.

As shown in FIG. 1, the distal portion 28 of the cutting catheter 14 may include serrated teeth 32 that can engage and break up a clot or occlusion when rotated in a clockwise/counterclockwise manner or in a forward/backward motion with regard to the cross-section of the vessel and the outer catheter 12. The teeth 32 may be formed integrally with the distal portion 28 of the cutting catheter 14 or may be formed of a different material, such as stainless steel or titanium, and attached to the distal portion 28 of the cutting catheter 14 by suitable methods of attachment, such as adhesives. The rotational or forward/backward motions are generally imparted manually by the fingers of the operating surgeon under fluoroscopic visualization, or by an electrical motor outside the patient's body (not shown).

The teeth 32 of the cutting catheter 14 are generally no more than about 4.0 mm in length. Moreover, the outer catheter 12 is generally no more than about 1.0 to about 4.0 mm shorter in length than the corresponding cutting catheter 14, to prevent the teeth 32 of the cutting catheter 14 from extending too far into the vessel, unprotected by the outer catheter. This embodiment provides protection against imparting damage to the vessel wall.

For intracranial applications (such as an acute stroke), the bypass catheter 16 may have a length from 150 cm to about 300 cm and may have an external diameter from 0.62 mm to 0.95 mm. The cutting catheter 14 may have an external diameter from about 0.60 mm to about 1.40 mm and the outer catheter 12 may have an external diameter from about from 0.75 mm to 1.75 mm. In general, the internal diameter of outer catheter 12 is proximate to the external diameter of cutting catheter 14, without an intermediate catheter, and will ideally have an internal diameter from about 0.10 mm to about 0.50 mm larger than the external diameter of the cutting catheter 14.

In one embodiment, the cutting catheter 14 may have an internal diameter from about 0.40 mm to about 1.17 mm, and the outer catheter 12 may have an internal diameter from about 0.75 mm to about 1.50 mm. Moreover, the cutting catheter 14 may have a length from about 130 cm to about 150 cm. However, it should be appreciated that catheters of any suitable dimensions may be used.

Cutting catheter 14, the bypass catheter 16, and at least one outer catheter 12, may be color-coded or numerically coded to form a matching system. All catheters that can be used together should be similarly coded to avoid any mismatch. It is contemplated that this feature would minimize potential complications of damage to the blood vessel wall that may occur if the cutting catheter 14 is significantly longer (more than 1-4 mm) than the outer catheter 12.

The outer catheter 12, cutting catheter 14, and the bypass catheter 16 may all be made of a metallic material, such as stainless steel or titanium, a plastic or polymeric material, or a combination of the two. Other suitable materials are also contemplated.

As referred to above, the revascularization catheter system 10 may also include one or more guidewires. The primary guidewire 18 may be coated with a hydrophilic substance and may be used for initial placement of the revascularization catheter system 10. The primary guidewire 18 may have a length from about 180 cm to about 190 cm. A second guidewire (not shown) may be used to exchange the coaxial catheters and may be similarly constructed and have a length of about 300 cm.

Figure 2:
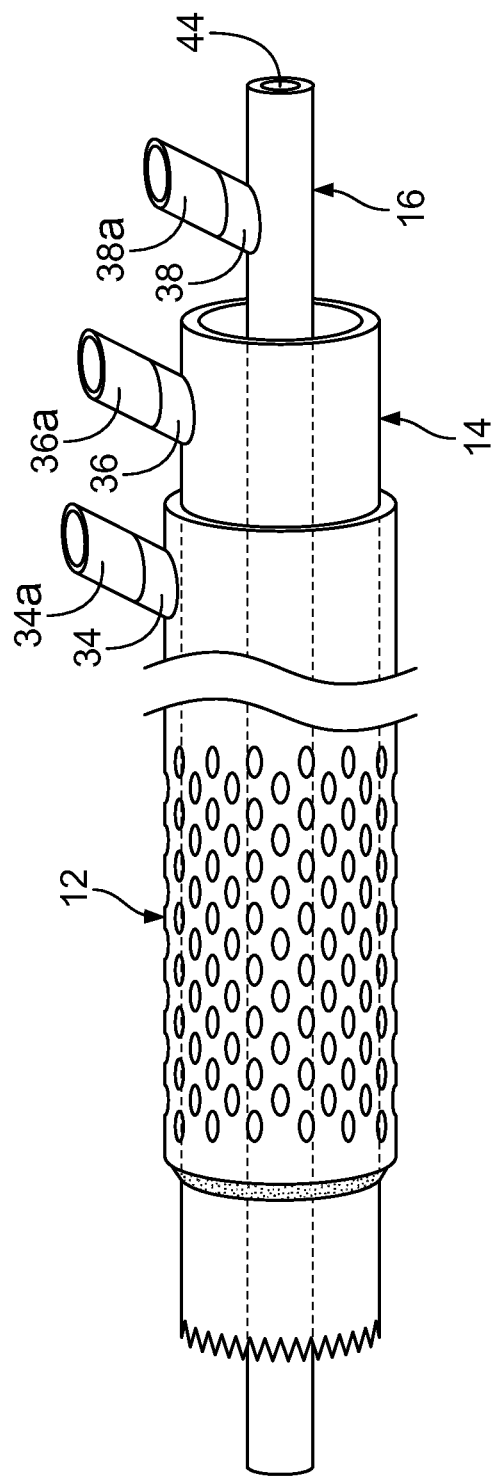
FIG. 2 is a side view of the proximal portion of the coaxial revascularization catheter of FIG. 1.

As shown in FIG. 2, the revascularization catheter system 10 may be introduced to a patient's body by inserting a bi-lumen sheath (not shown) into the patient's femoral artery. The revascularization catheter system 10, including the outer catheter 12, the cutting catheter 14, and the bypass catheter 16 may then be, in the case of a stroke patient, navigated through the first lumen of the sheath into the femoral artery, up and around the arch of the aorta, into the carotid or vertebral artery, to the skull base, and deployed at the site of the arterial occlusion in the cerebral arteries. A guidewire 18 may be used to deploy the coaxial catheters 12, 14, and 16.

It should be noted that while the bypass catheter 16, the cutting catheter 14, and outer catheter 12, are navigated through the body and positioned at the site of the occlusion, pressurized (at approximately 300 mm Hg) and/or heparinized saline is pumped through all of the lumen of the catheters 12, 14, and 16. The influx of the heparinized saline prevents blood and other potential debris, such as emboli, from entering and clogging the catheters. In one embodiment, the catheters each have at least one inlet portal, shown in FIG. 2 as 34, 36, and 38, that generally include luer locks. The inlet portals 34, 336, and 38 may be connected to a saline or other treatment solution source with rotating hemostatic valves 34a, 36a, and 38a, or other such suitable connection devices.

Figure 3:
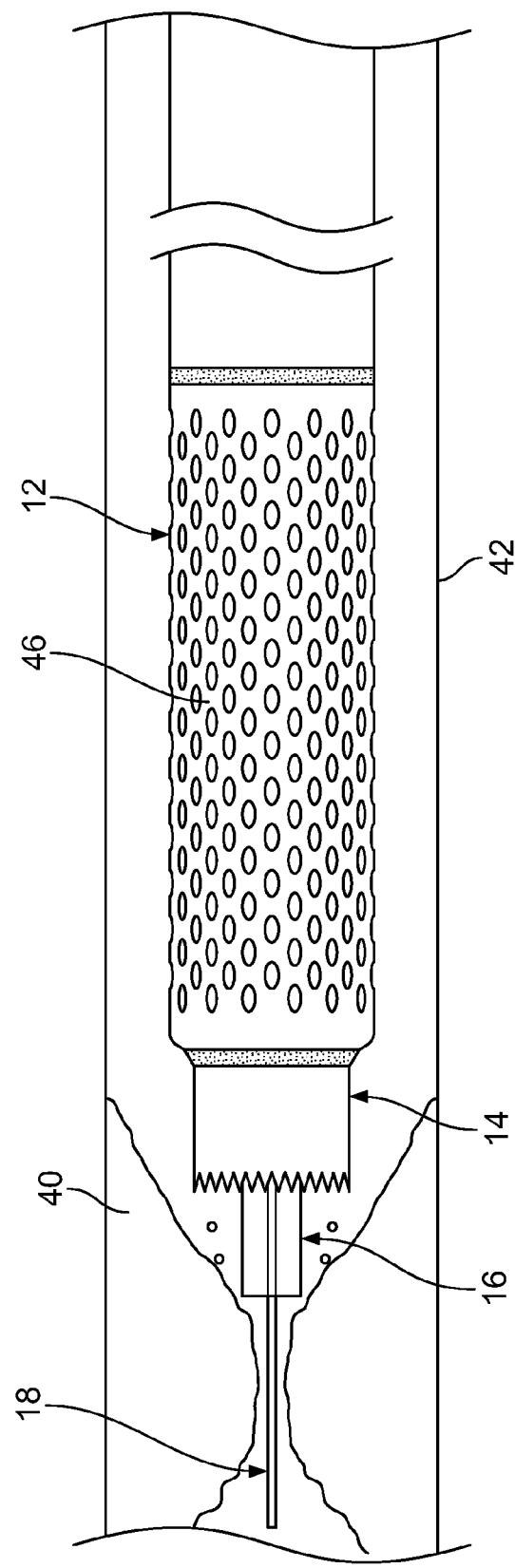
FIG. 3 is a side view of the coaxial revascularization catheter of FIG. 1 disposed at an obstruction site.
Figure 4:
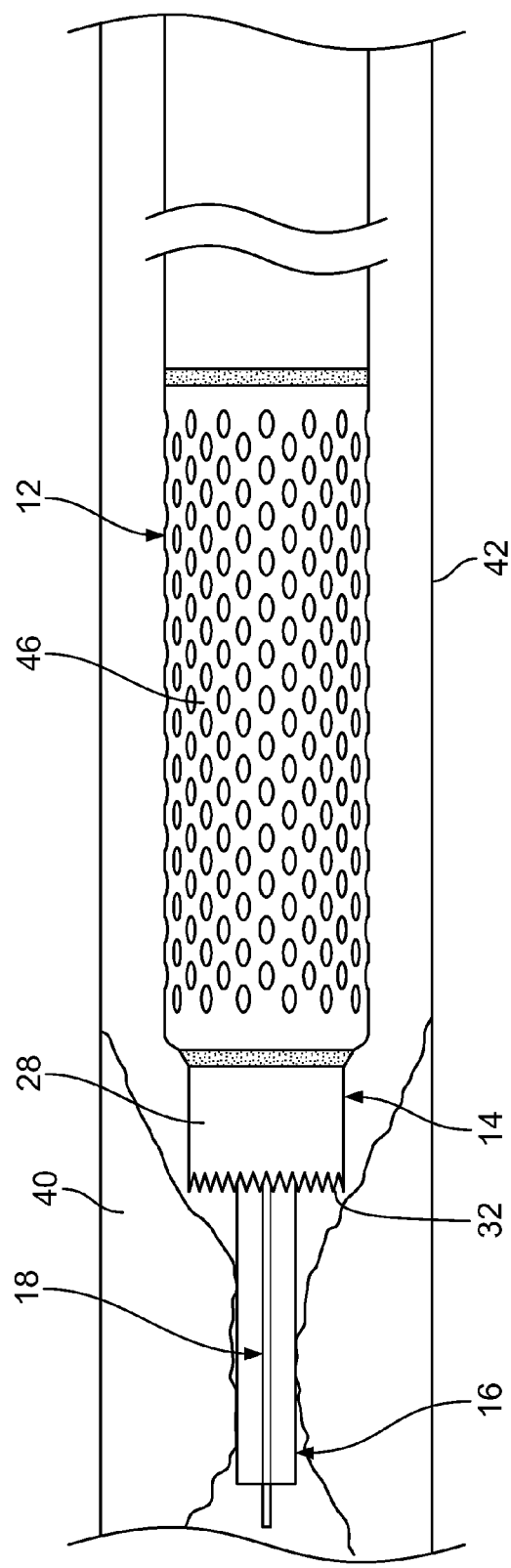
FIG. 4 is a side view of the coaxial revascularization catheter of FIG. 1 disposed at an obstruction site.

FIG. 3 and FIG. 4 show the revascularization catheter system 10 in successive positions in relation to an occlusion 40 in a vessel 42. FIG. 3 shows the bypass catheter 16 the cutting catheter 14, and the outer catheter 12 disposed within the vessel 42 and positioned at proximal portion of an occlusion 40, while a segment of the guidewire 18 extends through the occlusion 40. FIG. 4 shows a portion of the bypass catheter 16 extending through the occlusion 40 along the guidewire 18.

As shown in FIG. 4, the bypass catheter 16 may be advanced distally past the occlusion 40 to deliver arterialized blood beyond the offending obstruction to a blood starved region of the brain. By using the bypass catheter 16 to deliver blood to the brain, the amount of time that the physician has to reestablish blood flow to the patient's ischemic brain is increased dramatically.

Once the bypass catheter 16 is moved through the occlusion 40, the physician may begin to pump blood through the bypass catheter 16 to the portion of the brain that has been deprived due to an ischemic incident. The blood may be delivered to the bypass catheter 16 through second inlet opening 44 (as shown in FIG. 2). In one embodiment, a second (output) portal in the sheath (not shown) may be used to re-route blood from the femoral artery into the bypass catheter 16.

Alternatively, an injection of arterialized blood with heparinized pressurized saline may be administered through the bypass catheter 16 through the second inlet portal 44 by withdrawing the patient's own blood from the femoral artery into a syringe (not shown) and mixing the blood with heparinized saline.

Generally, the bypass catheter 16 may extend considerably (up to 10 cm) farther beyond the cutting catheter 14 and the outer catheter 12 in order to effectuate the bypass method. In addition to the arterialized blood, thrombolytic agents, cold plasma, and saline may be administered past the occlusion in the manner described above. The cold plasma may be used to create regionalized hypothermia, extending the time the surgeon may have to effectively remove the offending obstruction.

After delivering the arterialized blood through the bypass catheter 16 for approximately five minutes, the bypass catheter may be removed and cutting catheter 14 may be used to remove a core of the occlusion 40.

With rotational and axial movement of the teeth 32 at the distal portion 28 of the cutting catheter 14, the physician begins to sculpt a core section of the occlusion 40 and create small emboli. The torsional/rotational sculpting maneuver, in additional to the axial movement of the cutting catheter 14, facilitates the distal progress of the cutting catheter 14 into the vessel 42, continuously breaking up the offending occlusion 40. After the sculpting maneuver is performed, the cutting catheter 14, bypass catheter 16, and the primary guidewire 18 may be removed from the vessel 42, leaving the outer catheter 12 in place for delivery of medicine, blood, or other fluid to the ischemic portion of the vessel 42.

In this embodiment, once the physician begins to cut the occlusion 40, the pressurized saline within the cutting catheter 14 and the outer catheter 12 should be discontinued, so that the disrupted emboli are not flushed further into the vessel 42. A negative pressure may be applied to the lumen within the cutting catheter 14. The pressure may be imparted by a negative-pressure pump or by the operator, using a syringe with a flow-limiting valve. The negative pressure generated will generally be less than the pressure required to collapse the walls of the involved blood vessel.

In another embodiment, emboli created by the sculpting maneuver may also be treated using repeated doses of thrombolytic or platelet antagonist medication, depending on the nature of the obstruction. The medication may be delivered through the lumen of the cutting catheter 14.

The bypass procedure described above may be repeated for as many times as necessary, alternating the use of the cutting catheter 14 for about ten minutes with the use of the bypass catheter 16 to administer an arterialized blood mixture for about 5 minutes. Moreover, because the bypass catheter 16 and the cutting catheter 14 have separate and distinct lumina, the bypass catheter 16 may remain in place while the cutting catheter 14 is used to engage and remove at least a portion of the occlusion 40. Therefore, in another embodiment, the bypass catheter 16 may be made to function simultaneously with the use of the cutting catheter 14.

As shown in FIGS. 1 and 3-5, the distal portion 22 of the outer catheter 12 includes a diffusion portion 46 having multiple perforations 48. The perforations 48 provide fluid communication from the lumen of the outer catheter 12 to the vessel 42 wall. It is also contemplated that the perforations 46 may extend beyond the distal portion 22 of the outer catheter 12.

The outer catheter 12 is peripherally disposed around the cutting catheter 14 and may be closed at its distal portion 22. The closure of the distal portion 22 may be accomplished by tapering the distal portion 22 of the outer catheter 12 to meet the outer diameter of the cutting catheter 14. The cutting catheter 14, however, will still be rotatable within the outer catheter 12.

Referring again to FIG. 5, as the cutting catheter 14 is used to remove portions of the occlusion 40, the cutting catheter 14 and the outer catheter 12 may be moved distally within the vessel 42. As the cutting catheter 14 and outer catheter 12 are moved through the vessel 42, the diffusion portion 46 of the outer catheter 12 may be positioned within the occlusion 40 for the duration of the treatment. The diffusion portion 46 may also include radiographic markers 50a and 50b, as those shown in FIG. 5. The radiographic markers may include radiopaque rings or embedded pellets, among other suitable markers. Although it would be helpful to know a priori the length of the actual occlusion, not knowing the length does not limit the use of the revascularization catheter system 10, as it can become known simultaneously with initialization of thrombolysis.

Once the diffusion portion 46 of the outer catheter 12 is positioned within the occlusion 40, the negative pressure being applied to the lumen of the cutting catheter 14 can be discontinued so that a medicated treatment solution can be introduced directly to the remaining occlusion 40 through the diffusion portion 46 of the outer catheter 12. This system of localized, distributed administration of medication through the distal portion 22 of the cutting catheter 14 and the perforations 48 in the diffusion portion 46 exposes a greater surface area of the target occlusion 40 to the medicated treatment solution, such as a thrombolytic agent, antiplatelet agent, or nitrovasodilator (i.e. a nitric oxide-based medication). The localized delivery of thrombolytic agent, antiplatelet agent, or nitrovasodilator through the diffusion portion 46 will remove or reduce the size of the occlusion 40, thereby increasing the size of the lumen of the occluded vessel 42 to improve blood flow there through.

In the case of administration of nitric oxide-based vasodilator, the effect is one of distributing vasodilator medication to a segment of occluded vessel, allowing localized vasodilation and helping to liberate the vessel wall from the occlusive thrombus by allowing it to expand away from the latter.

The diffusion portion 46 may also be used to deliver intralesional medication, especially thrombolytic medication for dissolving the lesion, and/or vasodilator medication for increasing the width of the vessel 42 at the site of obstruction. The diffusion portion 46 also may be used to deliver medication, such as antiplatelet (2B3A glycoprotein receptor blocker) or vasodilator medication, to a chosen segment of a blood vessel.

Figure 5:
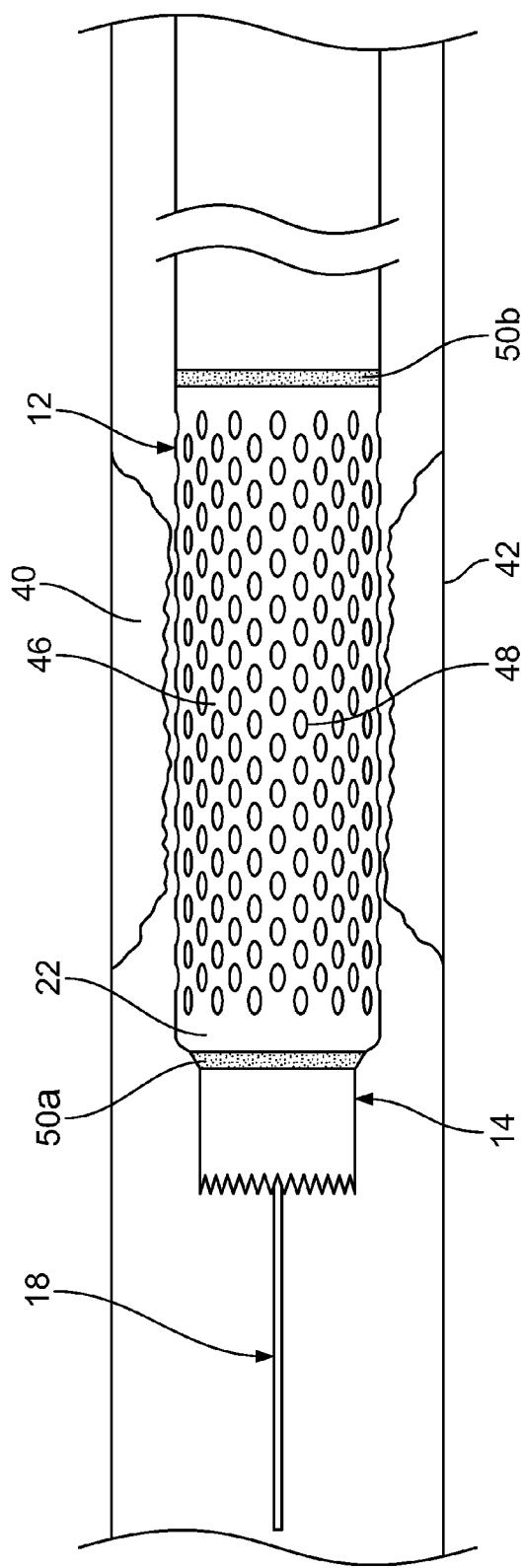
FIG. 5 is a side view of the coaxial revascularization catheter of FIG. 1 disposed at an obstruction site.

Once the revascularization catheter system 10, as shown in FIG. 5, has been used to remove a portion of the occlusion 40, the cutting catheter 14 may be used to impart localized fluid-mediated hypothermia by delivering a pressurized cooling solution beyond the occlusion. The solution may generally include a heparinized pressured saline and/or a blood/oxygenated compound that is delivered to produce localized regional hypothermia to the brain via the bloodstream. In this embodiment, the heparinized pressured saline component of the solution is cooled before it is introduced into the revascularization catheter system 10, either by itself or in combination with the oxygen-carrying compound (usually blood). It is contemplated that any suitable method of cooling the solution may be used, such as by a thermostat-controlled refrigeration device outside of the patient's body.

In another embodiment, after the cutting catheter 14 has removed a portion of the occlusion 40, the cutting catheter 14 may be removed and replaced with a second cutting catheter (not shown) of larger diameter within the outer catheter 12. In this manner, the core of occlusion 40 created by the cutting catheters may be progressively removed. This concept of removal of the cutting catheter 14 and its replacement with cutting catheters of ever-increasing outer diameter will create a progressive increase in luminal diameter in the blocked artery, while avoiding unnecessary disruption of the vessel 42 wall that is created by stripping portions of the occlusion 40 away in its entirety.

In yet another embodiment, the revascularization catheter system 10 shown in FIG. 1 can be constructed with a second outer catheter (not shown). The support provided by the triaxial arrangement allows the revascularization catheter system 10 to be used for distal penetration into a cerebral vessel. Once the revascularization catheter system 10 engages the offending occlusion 40 with the serrated distal portion 28 of the cutting catheter 14, the revascularization catheter system 10 can be disassembled by removing the second outer catheter, leaving only the first outer catheter 12, the cutting catheter 14, the bypass catheter 16, and the primary guidewire 18 disposed within the larger lumen of the first outer catheter 12. This embodiment provides a larger lumen through which the obstructing emboli can be aspirated or captured or through which specific medication may be delivered.

It is also contemplated that the revascularization catheter system 10 may be used without the bypass catheter 16. In addition, it is contemplated that the revascularization catheter system 10 may be used for both intracranial and peripheral (limb, ischemic bowel, organ ischemia) situations characterized by vascular insufficiency. One such embodiment may be used to treat cardiac ischemia, by insertion into a coronary artery and utilizing endovascular bypass, clot removal and localized medication delivery functions of the system. It may also be used in venous vasculature, for situations of venous obstruction or insufficiency.

Figure 6:
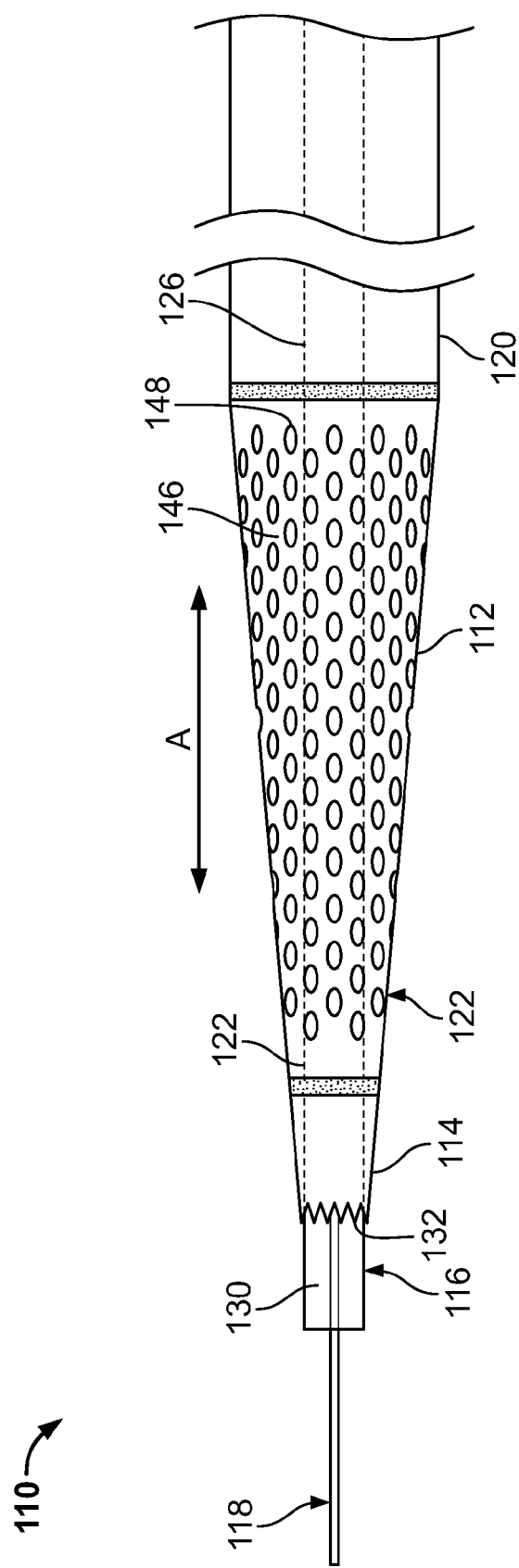
FIG. 6 is a side view of another embodiment of a coaxial revascularizaton catheter.
Figure 14:
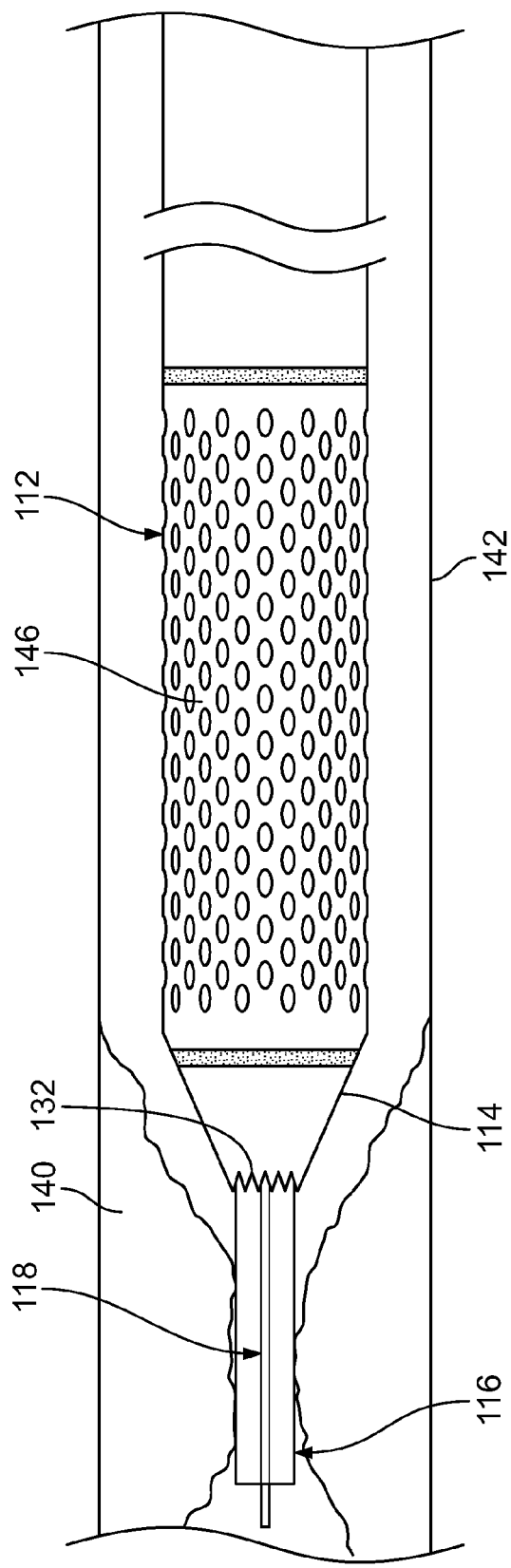
FIG. 14 is a side view of the coaxial revascularization catheter of FIG. 6 disposed at an obstruction site.

Referring to FIG. 6, in another embodiment, a revascularization catheter system 100 may include an outer catheter 112 with a cutting element 114, a bypass catheter 116, and a guidewire 118. In this embodiment, the outer catheter 112 includes a generally tubular body including a proximal portion 120, a transition portion (not shown), and a distal portion 122. The distal portion 122 of the outer catheter 112 also includes a diffusion portion 146 having multiple perforations 148. The perforations 148 provide fluid communication from the lumen of the outer catheter 112 to a vessel 142 wall, as shown in FIG. 14.

The bypass catheter 116 is also comprised of a generally tubular body including a proximal portion 126, a transition portion (not shown), and a distal portion 130. The tubular bodies of both the outer catheter 112 and the bypass catheter 116 have at least one lumen therein extending from a distal end of the tubular bodies to a proximal end of the tubular bodies.

In this embodiment, the bypass catheter 116 is disposed within the outer catheter 112 and is movable, rotatable, or slidable within the outer catheter 112 in a clockwise/counterclockwise direction and slidable in a forward/backward direction within the outer catheter 112 along a horizontal axis A.

Referring again to FIG. 6, the distal portion 122 of the outer catheter 112 may include a cutting element 114 at its distal end 132. The cutting element 114 includes serrated teeth that can engage and break up a clot or occlusion when the outer catheter 112 is rotated in a clockwise/counterclockwise manner or in a forward/backward motion with regard to the cross-section of the vessel. The teeth of the cutting element 114 are generally no more than about 4.0 mm in length. The cutting element 114 may be formed integrally with, or affixed separately to, the distal end 132 of the distal portion 122 of the outer catheter 112.

Figure 7:
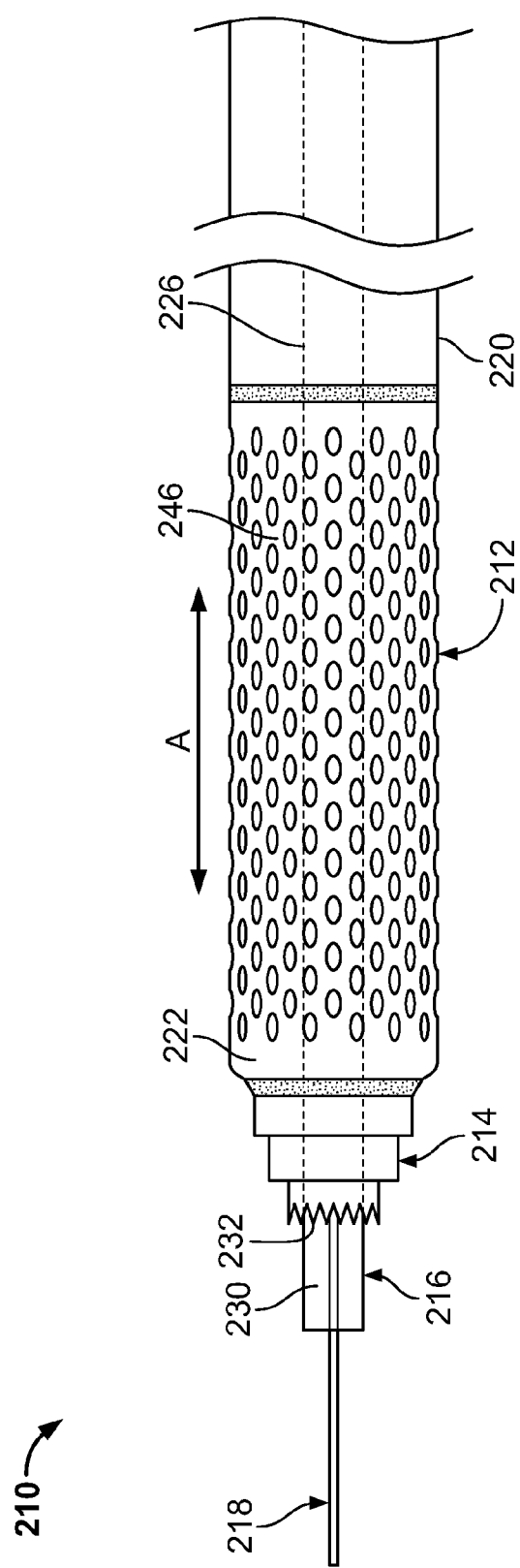
FIG. 7 is a side view of another embodiment of a coaxial revascularizaton catheter.

In this embodiment, the distal portion 122 of the outer catheter 112 is gradually tapered so that the inner diameter of the distal end 132 of the outer catheter 112 is only slightly larger than, approximately less than 1.0 mm, the outer diameter of the bypass catheter 116. Tapering the distal end 132 of the outer catheter 112 prevents fluid from exiting the distal end 132 of the outer catheter 112, directing the flow of a medicament through the perforations 148 instead. Tapering the distal portion of the outer catheter 112 so that it is flush with the outer diameter of the bypass catheter 116 also prevents the cutting element 114 from engaging the patient's vessel wall during a procedure. The distal portion may be gradually tapered, as shown in FIG. 6, or tapered in a stepped manner, as shown in FIG. 7.

Figure 8:
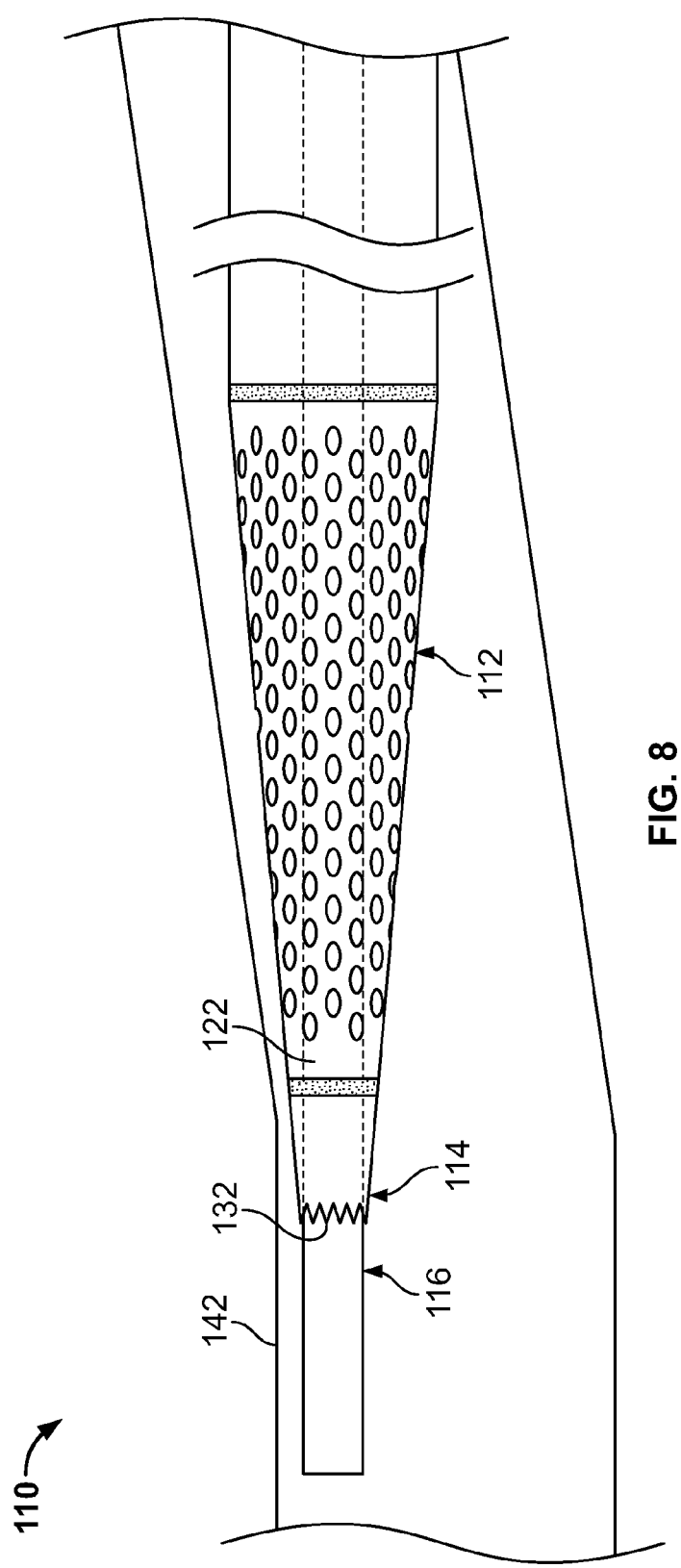
FIG. 8 is a side view of the revascularization catheter system of FIG. 6 deployed within the body.

In addition to tapering the distal portion 122 of the outer catheter 112, in practice the bypass catheter 116 extends beyond the distal end 132 of the outer catheter a minimum distance D, about 5 mm to about 7 mm, as shown in FIG. 8. By maintaining the minimum distance, the bypass catheter will prevent the cutting element 114 on the distal end 132 of the outer catheter 112 from cutting the vessel wall 142 of the patient as the revascularization catheter system 110 is moved to the site of the obstruction. By maintaining a minimum distance D, about 5.0 mm from the distal end of the bypass catheter 116 to the distal end 132 of the outer catheter 112, the vessel wall 142 will be pushed away from the cutting element 114 as the revascularization catheter system 110 moves through bends in the vessel.

Figure 9:
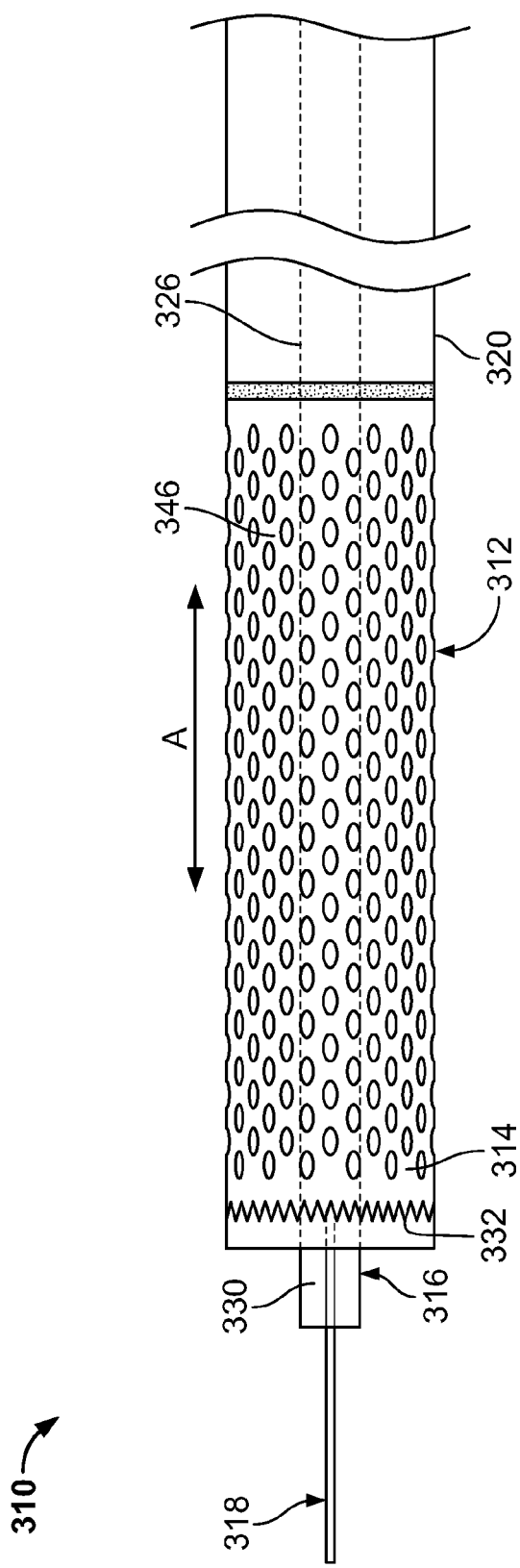
FIG. 9 is a side view of an alternative embodiment of a coaxial revascularizaton catheter.
Figure 10:
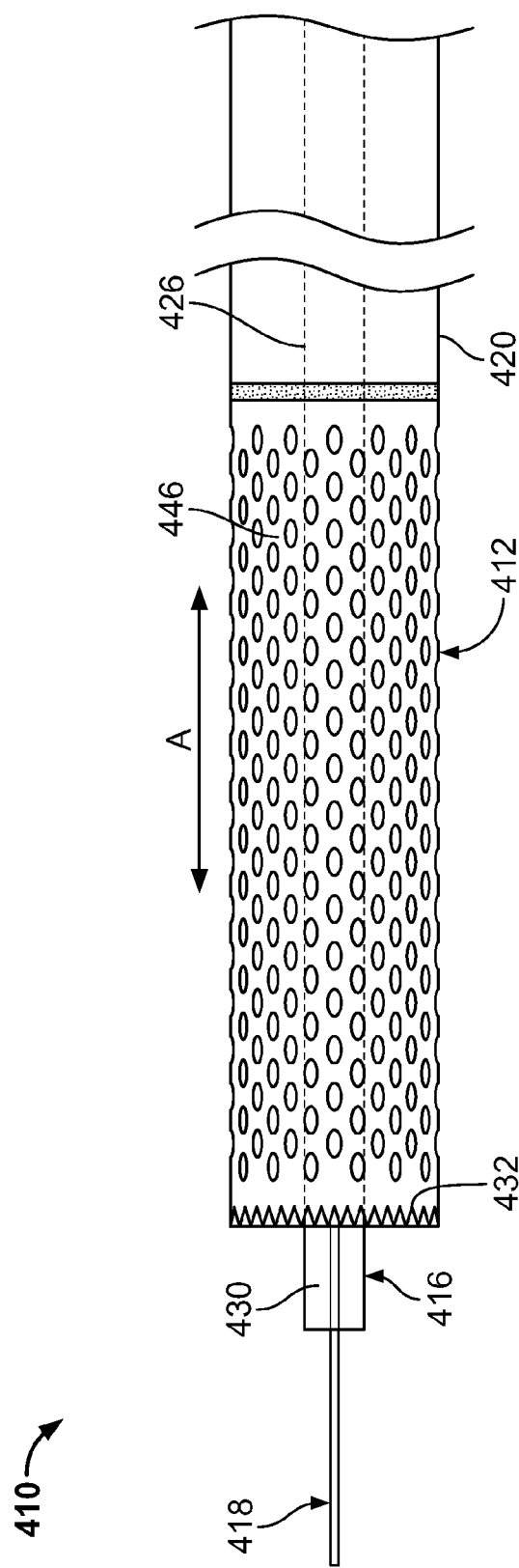
FIG. 10 is a side view of an alternative embodiment of a coaxial revascularizaton catheter.
Figure 11:
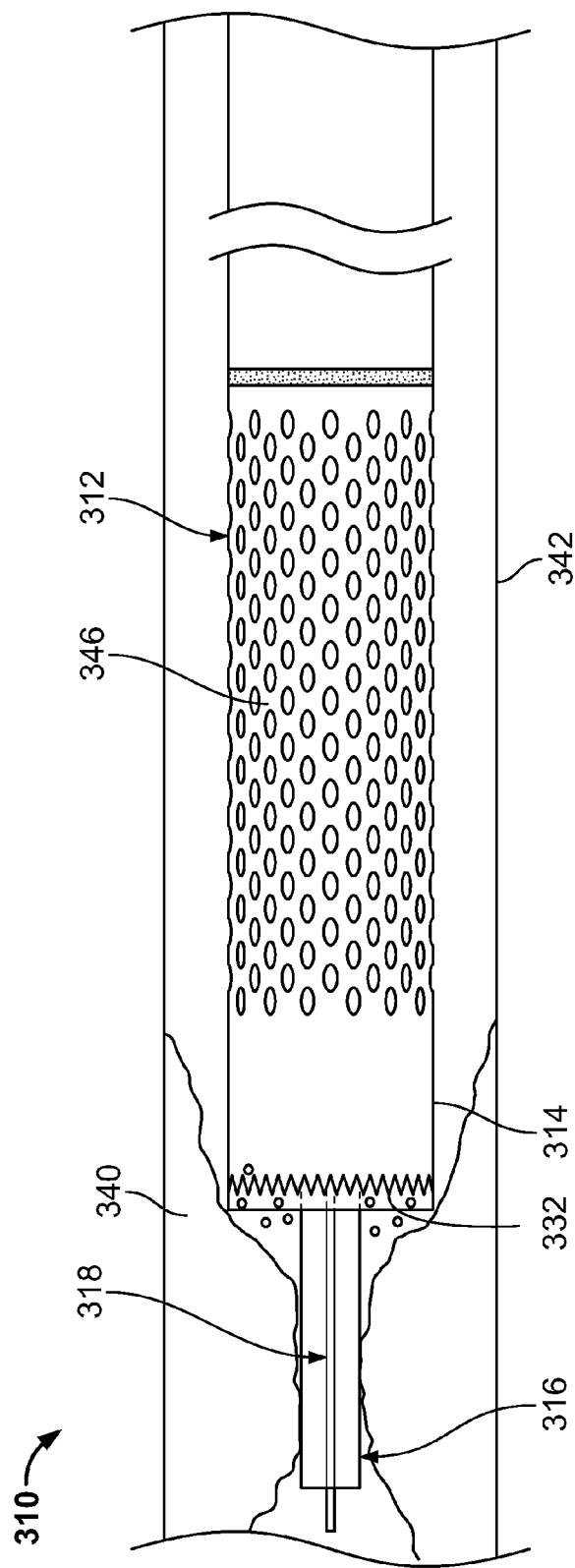
FIG. 11 is a side view of the coaxial revascularization catheter of FIG. 9 disposed at an obstruction site.

In other embodiments, as shown in FIGS. 9-12, the cutting element is a discrete part that is fixed internal to the distal end of the outer catheter. As shown in FIG. 9, the cutting element 314 may be slightly recessed within the distal end 332 of the outer catheter 312, such that it cannot independently engage the wall of the vessel. In yet another embodiment, as shown in FIG. 10, the cutting element 414 may be suspended radially from, or attached directly to (not shown), the inner wall of the outer catheter 412. In these embodiments, the cutting element 314 or 414 may engage the obstruction by gradually advancing the distal end 332 or 432 of the outer catheter 312 or 412 through the obstruction, as shown in FIG. 11 with reference to revascularization catheter system 310, for example.

Figure 12:
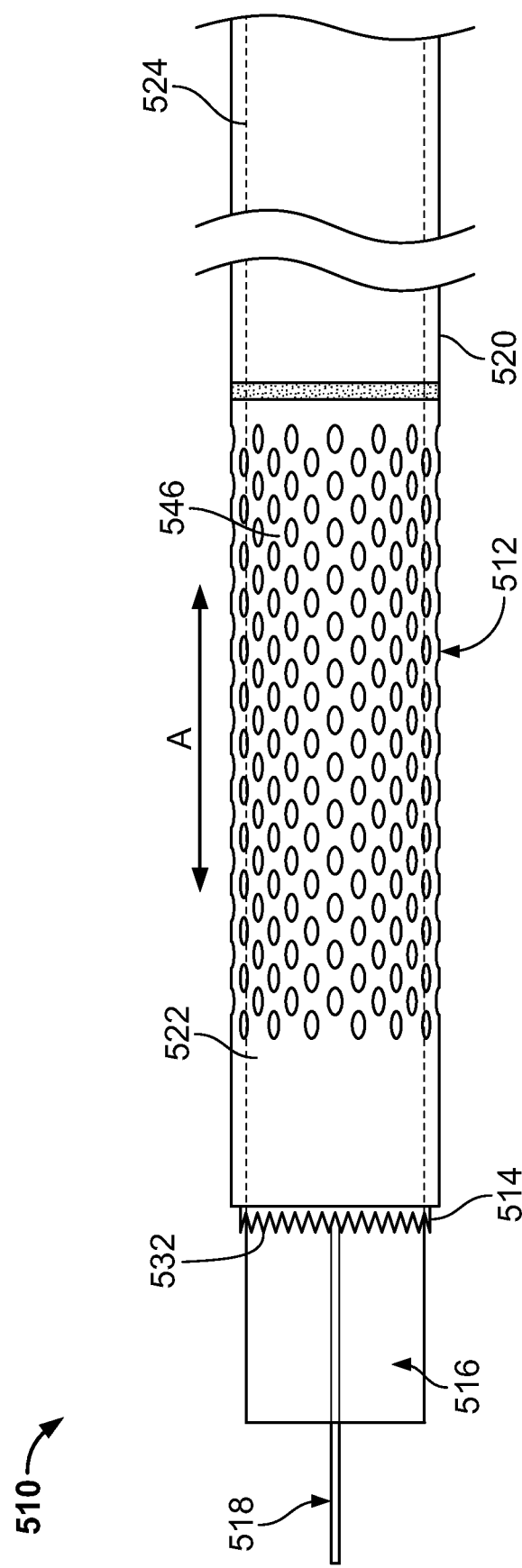
FIG. 12 is a side view of an alternative embodiment of a coaxial revascularizaton catheter.

In another embodiment, as shown in FIG. 12, the cutting element 514 may be affixed to the inside of, and extend slightly beyond, the distal end 532 of the outer catheter 512. The cutting element 514 may extend approximately 1 mm to about 5 mm beyond the distal end 532. In this embodiment the cutting element 514 may have an internal diameter that fits snugly around the bypass catheter 516 so that the cutting element does not engage the vessel wall during placement of the revascularization catheter system 510.

It should be appreciated that any of the embodiments shown in FIGS. 6-12 are contemplated for intracranial applications (such as an acute stroke). Referring, for example, to the embodiment shown in FIG. 6, the bypass catheter 116 may have a length from 150 cm to about 300 cm and may have an external diameter from 0.62 mm to 0.95 mm. In general, the internal diameter of outer catheter 112 is proximate to the external diameter of bypass catheter 116, and will ideally have an internal diameter from about 0.10 mm to about 0.50 mm larger than the external diameter of the bypass catheter 116. It should be appreciated that catheters of any suitable dimensions may be used.

The bypass catheter 116, and the outer catheter 112, may be color-coded or numerically coded to form a matching system. All catheters that can be used together should be similarly coded to avoid any mismatch. It is contemplated that this feature would minimize potential complications of damage to the blood vessel wall that may occur if the bypass catheter 116 is not long enough to provide the minimum distance from the distal end 132 of the outer catheter 112, as discussed above.

The outer catheter 112, cutting element 114, and the bypass catheter 116 may all be made of a metallic material, such as stainless steel or titanium, a plastic or polymeric material, or a combination of the two. Other suitable materials are also contemplated.

As referred to above, the revascularization catheter system 110 may also include one or more guidewires. The primary guidewire 118 may be coated with a hydrophilic substance and may be used for initial placement of the revascularization catheter system 110. The primary guidewire 118 may have a length from about 180 cm to about 190 cm. A second guidewire (not shown) may be used to exchange the coaxial catheters and may be similarly constructed and have a length of about 300 cm.

Figure 13:
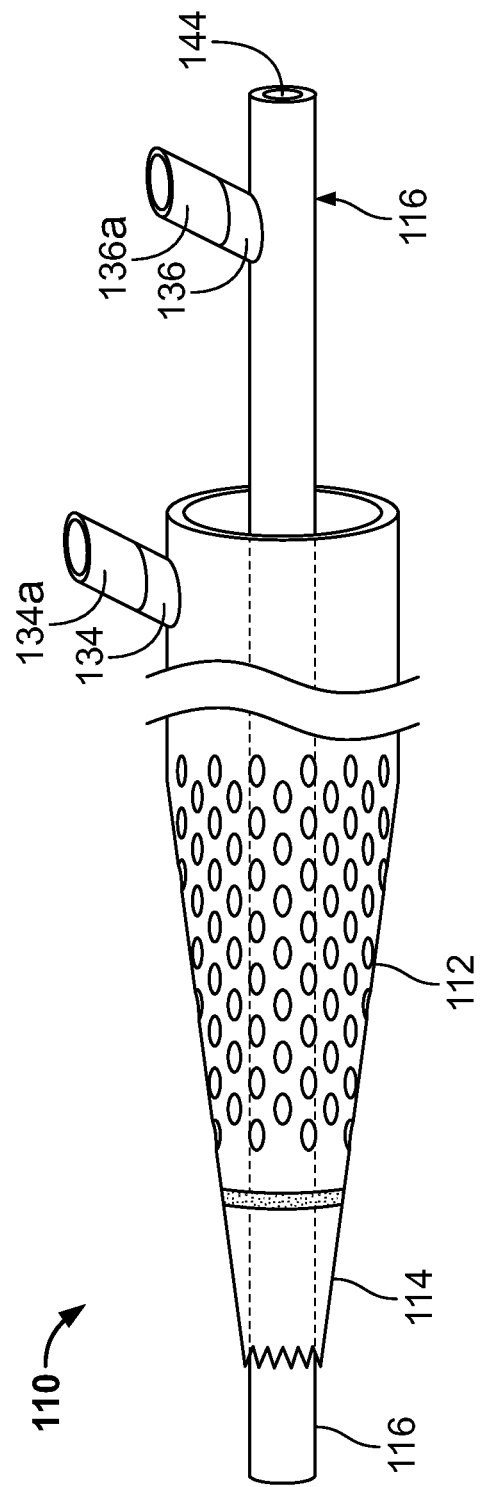
FIG. 13 is a side view of the proximal portion of the coaxial revascularization catheter of FIG. 6.

As shown in FIG. 13, the revascularization catheter system 110, for example as shown in FIG. 6, may be introduced to a patient's body by inserting a bi-lumen sheath (not shown) into the patient's femoral artery. The revascularization catheter system 110, including the outer catheter 112, the cutting element 114, and the bypass catheter 116 may then be, in the case of a stroke patient, navigated through the first lumen of the sheath into the femoral artery, up and around the arch of the aorta, into the carotid or vertebral artery, to the skull base, and deployed at the site of the arterial occlusion in the cerebral arteries. A guidewire 118 (not shown) may be used to deploy the system 110.

It should be noted that while the bypass catheter 116 and outer catheter 112, are navigated through the body and positioned at the site of the occlusion, pressurized (at approximately 300 mm Hg) and/or heparinized saline is pumped through both lumen of the catheters 112 and 116. The influx of the heparinized saline prevents blood and other potential debris, such as emboli, from entering and clogging the catheters. In one embodiment, the catheters each have at least one inlet portal 134 and 136, that generally include luer locks. The inlet portals 134 and 136 may be connected to a saline or other treatment solution source with rotating hemostatic valves 134a and 136a or other such suitable connection devices.

Figure 15:
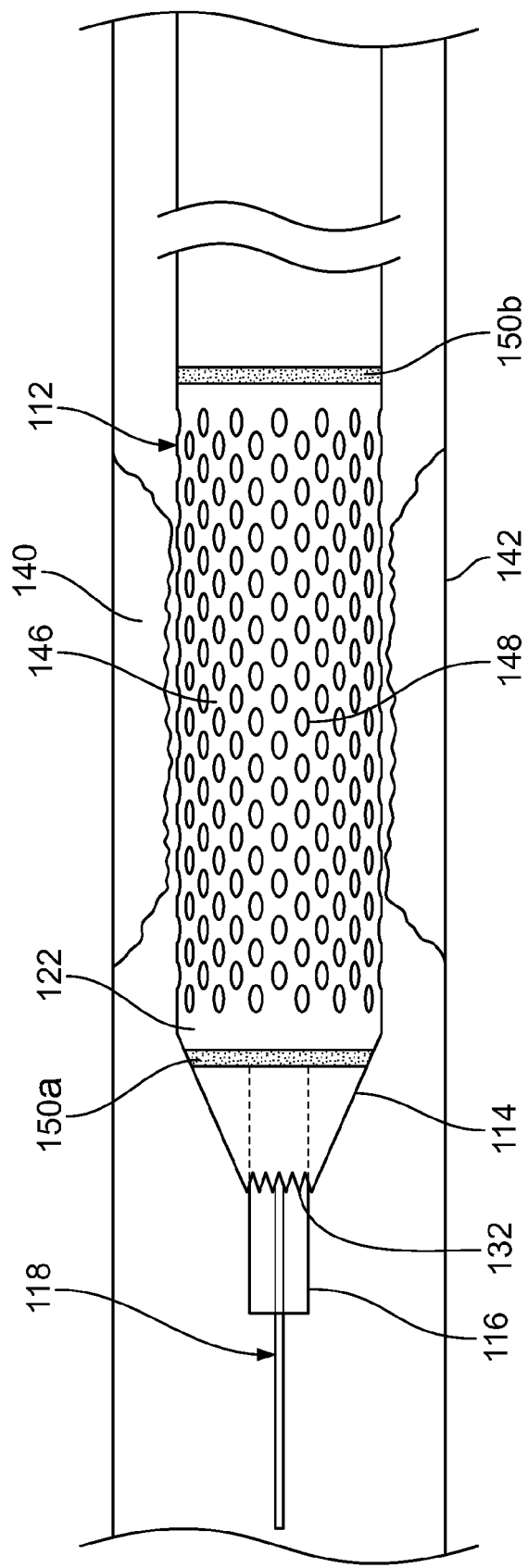
FIG. 15 is a side view of the coaxial revascularization catheter of FIG. 6 disposed at an obstruction site.

FIGS. 14 and 15 show the revascularization catheter system 110 in successive positions in relation to an occlusion 140 in a vessel 142. FIG. 14 shows the bypass catheter 116 and the outer catheter 112 disposed within the vessel 142 and positioned at proximal portion of an occlusion 140, while a segment of the guidewire 118 and the bypass catheter 116 extends through the occlusion 140.

As shown in FIG. 14, the bypass catheter 116 may be advanced distally past the occlusion 140 to deliver arterialized blood beyond the offending obstruction to a blood starved region of the brain. By using the bypass catheter 116 to deliver blood to the brain, the amount of time that the physician has to reestablish blood flow to the patient's ischemic brain is increased dramatically.

Once the bypass catheter 116 is moved through the occlusion 140, the physician may begin to pump blood through the bypass catheter 116 to the portion of the brain that has been deprived due to an ischemic incident. The blood may be delivered to the bypass catheter 116 through second inlet opening 144 (as shown in FIG. 13). In one embodiment, a second (output) portal in the sheath (not shown) may be used to re-route blood from the femoral artery into the bypass catheter 116.

Alternatively, an injection of arterialized blood with heparinized pressurized saline may be administered through the bypass catheter 116 through the second inlet portal 144 by withdrawing the patient's own blood from the femoral artery into a syringe (not shown) and mixing the blood with heparinized saline.

Generally, the bypass catheter 116 may extend considerably (up to 10 cm) farther beyond the outer catheter 112 in order to effectuate the bypass method. In addition to the arterialized blood, thrombolytic agents, cold plasma, and saline may be administered past the occlusion in the manner described above. The cold plasma may be used to create regionalized hypothermia, extending the time the surgeon may have to effectively remove the offending obstruction.

Optionally, after delivering the arterialized blood through the bypass catheter 116 for approximately five minutes, the bypass catheter 116 may be removed and the cutting element 114 on the outer catheter 112 may be used to remove a core of the occlusion 140. It is also contemplated that the bypass catheter 116 may remain in place during the sculpting maneuver, as discussed below.

As shown in FIG. 15, with rotational and axial movement of the teeth at the distal end 132 of the cutting element 114, the physician begins to sculpt a core section of the occlusion 140 and create small emboli. The torsional/rotational sculpting maneuver, in additional to the axial movement of the cutting element 114, facilitates the distal progress of the outer catheter 112 into the vessel 142, continuously breaking up the offending occlusion 140. After the sculpting maneuver is performed, the bypass catheter 116 and the primary guidewire 118 may be removed from the vessel 142, leaving the outer catheter 112 in place for delivery of medicine, blood, or other fluid to the ischemic portion of the vessel 142 through its multiple perforations 148.

In this embodiment, once the physician begins to cut the occlusion 140, the pressurized saline within the outer catheter 112 should be discontinued, so that the disrupted emboli are not flushed further into the vessel 142. A negative pressure may be applied to the lumen within the outer catheter 114. The pressure may be imparted by a negative-pressure pump or by the operator, using a syringe with a flow-limiting valve. The negative pressure generated will generally be less than the pressure required to collapse the walls of the involved blood vessel.

In another embodiment, emboli created by the sculpting maneuver may also be treated using repeated doses of thrombolytic or platelet antagonist medication, depending on the nature of the obstruction. The medication may be delivered through the lumen of the outer catheter 114.

The bypass procedure described above may be repeated for as many times as necessary, alternating the use of the cutting element 114 for about ten minutes with the use of the bypass catheter 116 to administer an arterialized blood mixture for about 5 minutes. Moreover, because the bypass catheter 116 and the outer catheter 112 have separate and distinct lumina, the bypass catheter 116 may remain in place while the outer catheter 112 is used to engage and remove at least a portion of the occlusion 140. Therefore, in another embodiment, the bypass catheter 116 may be made to function simultaneously with the use of the outer catheter 112.

As the cutting element 112 is used to remove portions of the occlusion 140, the outer catheter 112 may be moved distally within the vessel 142. As the outer catheter 112 are moved through the vessel 142, the diffusion portion 146 of the outer catheter 112 may be positioned within the occlusion 140 for the duration of the treatment. The diffusion portion 146 may also include radiographic markers 150a and 150b. The radiographic markers may include radiopaque rings or embedded pellets, among other suitable markers. Although it would be helpful to know a priori the length of the actual occlusion, not knowing the length does not limit the use of the revascularization catheter system 110, as it can become known simultaneously with initialization of thrombolysis.

Once the diffusion portion 146 of the outer catheter 112 is positioned within the occlusion 140, the negative pressure being applied to the lumen of the outer catheter 112 can be discontinued so that a medicated treatment solution can be introduced directly to the remaining occlusion 140 through the diffusion portion 146 of the outer catheter 112. This system of localized, distributed administration of medication through the distal portion 122 of the outer catheter 112 and the perforations 148 in the diffusion portion 146 exposes a greater surface area of the target occlusion 140 to the medicated treatment solution, such as a thrombolytic agent, antiplatelet agent, or nitrovasodilator (i.e. a nitric oxide-based medication). The localized delivery of thrombolytic agent, antiplatelet agent, or nitrovasodilator through the diffusion portion 146 will remove or reduce the size of the occlusion 140, thereby increasing the size of the lumen of the occluded vessel 142 to improve blood flow there through.

In the case of administration of nitric oxide-based vasodilator, the effect is one of distributing vasodilator medication to a segment of occluded vessel, allowing localized vasodilation and helping to liberate the vessel wall from the occlusive thrombus by allowing it to expand away from the latter.

The diffusion portion 146 may also be used to deliver intralesional medication, especially thrombolytic medication for dissolving the lesion, and/or vasodilator medication for increasing the width of the vessel 142 at the site of obstruction. The diffusion portion 146 also may be used to deliver medication, such as antiplatelet (2B3A glycoprotein receptor blocker) or vasodilator medication, to a chosen segment of a blood vessel.

Once the revascularization catheter system 110, as shown in FIG. 16, has been used to remove a portion of the occlusion 140, the outer catheter 116 may be used to impart localized fluid-mediated hypothermia by delivering a pressurized cooling solution beyond the occlusion. The solution may generally include a heparinized pressured saline and/or a blood/oxygenated compound that is delivered to produce localized regional hypothermia to the brain via the bloodstream. In this embodiment, the heparinized pressured saline component of the solution is cooled before it is introduced into the revascularization catheter system 110, either by itself or in combination with the oxygen-carrying compound (usually blood). It is contemplated that any suitable method of cooling the solution may be used, such as by a thermostat-controlled refrigeration device outside of the patient's body.

In another embodiment, after the outer catheter 112 has removed a portion of the occlusion 140, the outer catheter 112 may be removed and replaced with a second outer catheter (not shown) of larger diameter. In this manner, the core of occlusion 140 created by the cutting elements may be progressively removed. This concept of removal of the outer catheter 112 and its replacement with catheters of ever-increasing outer diameter will create a progressive increase in luminal diameter in the blocked artery, while avoiding unnecessary disruption of the vessel 142 wall that is created by stripping portions of the occlusion 140 away in its entirety.

It is also contemplated that the revascularization catheter system 10 may be used without the bypass catheter 116. In addition, it is contemplated that the revascularization catheter system 110 may be used for both intracranial and peripheral (limb, ischemic bowel, organ ischemia) situations characterized by vascular insufficiency. One such embodiment may be used to treat cardiac ischemia, by insertion into a coronary artery and utilizing endovascular bypass, clot removal and localized medication delivery functions of the system. It may also be used in venous vasculature, for situations of venous obstruction or insufficiency.

While example methods and compositions have been illustrated by describing examples, and while the examples have been described in considerable detail, it is not the intention of the applicant to restrict or in any way limit the scope of the appended claims to such detail. It is, of course, not possible to describe every conceivable combination of components or methodologies for purposes of describing the systems, methods, devices, and so on, described herein. Additional advantages and modifications will readily appear to those skilled in the art. Therefore, the invention is not limited to the specific details, the representative revascularization catheter systems, and illustrative examples shown and described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

The invention claimed is:

1. A catheter system for alleviating cerebral vascular blockage comprising:
    an outer catheter;
    a bypass catheter comprising a distal end portion, a proximal end portion, an inner lumen, and a continuous outer surface that is substantially free of apertures and is configured to deliver fluid from an opening the proximal end to an opening in the distal end;
    wherein the bypass catheter is slidably disposed within the outer catheter, and
    wherein the outer catheter comprises a cutting element with serrated teeth at its distal end portion and plurality of perforations through a side-wall of the distal end portion to provide fluid communication from the lumen of outer catheter to the vessel wall.

2. The catheter system of claim 1, wherein the serrated distal end comprises a plurality of teeth having a length of between about 1.0 mm and about 4.0 mm.

3. The catheter system of claim 1, wherein the bypass catheter has a length that is greater than a length of the outer catheter, and wherein the bypass catheter is a microcatheter.

4. The catheter system of claim 1, wherein the distal end portion of the outer catheter is tapered from a first diameter to a second diameter.

5. The catheter system of claim 4, wherein the distal end portion of the outer catheter is gradually tapered from a first diameter to a second diameter.

6. The catheter system of claim 4, wherein the distal portion of the outer catheter is gradually tapered.

7. The catheter system of claim 1, wherein the serrated teeth of the cutting element extend beyond the distal end of the outer catheter.

8. The catheter system of claim 1, wherein the distal end of the outer catheter extends beyond the serrated teeth of the cutting element.

9. The catheter system of claim 1, wherein the catheter system is configured to attach a negative pressure pump to a proximal portion of the outer catheter.

10. A method of removing cerebral vascular blockage comprising:
    providing a catheter system comprising an outer catheter comprising a cutting element with serrated teeth and a bypass catheter comprising a distal end, a proximal end, an inner lumen, and a continuous outer surface that is substantially free of apertures and is configured to deliver fluid from an opening in the proximal end of the bypass catheter to an opening in the distal end,
    wherein the bypass catheter is slidably disposed within the outer catheter;
    positioning a distal portion of the catheter system at a proximal end of an occlusion located within a cerebral vessel;

moving the bypass catheter through the occlusion and delivering a medicated treatment solution through the bypass catheter;

moving the cutting element in a forward and backward motion, along a horizontal axis, to engage the occlusion and to create a removable portion of the occlusion; and removing the removable portion of the occlusion from the vessel, wherein the outer catheter comprises a distal portion and wherein the distal portion of the outer catheter comprises at least one perforation through a sidewall of the distal portion.

11. The method of claim 10, and wherein the method further comprises delivering a medicated treatment solution to the occlusion through the at least one perforation.

12. The method of claim 11, wherein the medicated treatment solution is selected from a solution of arterialized blood, cooled saline, thrombolytic agents, vasodilators, or a combination thereof.

13. The method of claim 10, wherein the method further comprises removing the removable portion of the occlusion by applying negative pressure.

14. The method of claim 13, wherein the method further comprises applying negative pressure to the catheter system manually with a flow-limiting syringe aspirator.

15. The method of claim 13, wherein the method further comprises applying negative pressure to the catheter system with a negative pressure pump.

* * * * *